(12) United States Patent  
Chivers

(10) Patent No.: US 6,307,013 B1  
(45) Date of Patent: Oct. 23, 2001

(54) CLARIFICATION OF PROTEIN PRECIPITATE SUSPENSIONS USING ANIONIC POLYMERIC FLOCCULANTS

(75) Inventor: Mark L. Chivers, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 09/354,493

(22) Filed: Jul. 16, 1999

Related U.S. Application Data

(60) Provisional application No. 60/093,555, filed on Jul. 21, 1998.

(51) Int. Cl.$^7$ ............... A61K 38/31; C07K 1/14; C07K 1/30
(52) U.S. Cl. ............ 530/311; 530/421; 514/806
(58) Field of Search .................... 530/421, 311

(56) References Cited

U.S. PATENT DOCUMENTS

| | | |
|---|---|---|
| 3,695,999 | 10/1972 | Forgione et al. |
| 3,956,519 * | 5/1976 | Evans et al. .............. 426/48 |
| 4,013,555 | 3/1977 | Davis ...................... 210/51 |
| 4,055,469 | 10/1977 | Snoke et al. ............. 195/66 |
| 4,208,282 * | 6/1980 | Becker .................... 210/44 |
| 4,271,028 | 6/1981 | Marfurt et al. .......... 210/727 |
| 4,382,028 | 5/1983 | Paget ..................... 260/112 |
| 4,511,502 | 4/1985 | Builder et al. .......... 260/111 R |
| 4,599,390 | 7/1986 | Fan et al. ............... 526/240 |
| 4,634,673 | 1/1987 | Johnson et al. ......... 435/234 |
| 4,645,829 | 2/1987 | Ho ......................... 530/344 |
| 4,652,630 | 3/1987 | Bentle et al. ........... 530/344 |
| 4,761,472 | 8/1988 | Schultze ................. 540/145 |
| 5,047,511 | 9/1991 | Mehrotra ................. 530/399 |
| 5,182,369 | 1/1993 | Storrs et al. ............ 530/667 |
| 5,413,720 | 5/1995 | Miller .................... 210/725 |
| 5,543,058 | 8/1996 | Miller .................... 210/725 |
| 5,551,316 | 9/1996 | Savage ................... 435/261 |

FOREIGN PATENT DOCUMENTS

| | | | |
|---|---|---|---|
| EP 57273 | 8/1982 | (DE) | ............... A23C/21/00 |
| 581 002 | 2/1994 | (EP) . | |

OTHER PUBLICATIONS

F.A.P Garcia, (Chapter 12—Protein Purification), In *Recovery Process for Biological Materials* edited by John F. Kennedy and Joaquin M. S. Cabral, 1993 John Wiley & Sons Ltd, pp. 355–367.

Halverson, F, Panzer, H. P. Kirk–Othmer Encycl. Chem. Technol., 3rd Ed. (1980), vol. 10, 489–523. Editor(s): Grayson, Martin; Eckroth, David. Publisher: Wiley, New York, N.Y.*

Database CaPlus, DN 97:180612, EP 57273, Nov. 1981.*

* cited by examiner

*Primary Examiner*—Michael Borin  
(74) *Attorney, Agent, or Firm*—George R. Beck; Howrey Simon Arnold & White, LLP

(57) ABSTRACT

Protein suspensions comprising soluble and insoluble components are purified via flocculation with anionic polymers, such as polyacrylamides, potato starch, or modified cellulose. The procedure improves the efficiency of solid/liquid separations and can minimize or eliminate the requirement for centrifugation and/or filtration in large scale biotechnological processes. The method is particularly well suited for the purification and clarification of protein suspensions containing soluble somatotropin monomer using polyacrylamide and polysaccharide flocculants.

35 Claims, 3 Drawing Sheets

CLARIFICATION OF PROTEIN PRECIPITATE SUSPENSIONS USING ANIONIC POLYMERIC FLOCCULANTS

This is a conversion of provisional application Ser. No. 60/093,555 filed Jul. 21, 1998.

BACKGROUND OF THE INVENTION

The present invention relates generally to the purification of proteins produced by recombinant DNA technologies. More particularly, it concerns the clarification of protein suspensions containing soluble and insoluble components via flocculation with anionic polymers.

The use of flocculating agents has been described in several industrial settings, including the biotechnology industry. For example, U.S. Pat. No. 5,047,511 describes the use of cationic flocculating agents in the recovery of recombinant somatotropin protein from a protein solution containing soluble high molecular weight contaminating proteins. This involved the selective precipitation of contaminating high molecular weight proteins by adding a cationic flocculant containing quaternary ammonium groups and then recovering the somatotropin from the solution.

Somatotropins, also known as growth hormones, are polypeptides produced and secreted by cells of the pituitary gland. These proteins are known to be effective in promoting pre-adult skeletal growth and meat production of beef cattle and swine, and can be produced reliably and inexpensively in large quantities by recombinant DNA technology. In addition, they are known to affect a variety of metabolic processes including the stimulation of lactation, improvements of the efficiency of converting feed to meat or milk, lipid-mobilizing effects, and others.

Recombinant DNA technology provides a means for the large scale production of heterologous proteins of interest in bacterial host cells. In the case of somatotropin, a growth hormone, the protein is sequestered in inclusion bodies within the cytoplasm of the host cells. The inclusion bodies can be recovered from the host cell culture by disrupting the cell so as to release the inclusion bodies, and thereafter collecting the inclusion bodies as a solid pellet by differential centrifugation. The inclusion bodies are solubilized in an aqueous solution of a suitable chaotropic agent such as urea or guanidine hydrochloride at an alkaline pH and subsequently naturized by contact with a mild oxidizing agent to form intramolecular disulfide bonds and to refold the protein into its biologically active, native conformation. Methods for the solubilization and naturation of somatotropin protein produced by E. coli bacteria are described in U.S. Pat. Nos. 4,511,502 and 4,652,630, each of which is incorporated herein by reference.

The somatotropin refold solution obtained from the naturation step (as described for example in U.S. Pat. Nos. 4,511,502 and 4,652,630) comprises an aqueous solution of somatotropin monomers, dimers and higher oligomers, along with residue and other debris from the host cells. Of these, the somatotropin monomer is the desired biologically active agent. U.S. Pat. No. 5,182,369, the disclosure of which is incorporated herein by reference, describes the selective precipitation of somatotropin dimer and higher oligomers together with residual host cell proteins and other contaminating substances from a pH-adjusted somatotropin refold solution, leaving the desired somatotropin monomer as the primary soluble constituent of the suspension.

Once the somatotropin oligomers and other contaminants have been selectively precipitated using this approach, it is necessary to remove the precipitated proteins and other insoluble contaminants from the suspension in order to obtain somatotropin monomers of the desired purity. Such liquid/solid separations as those required for this purification step are employed in most industrial biotechnological processes and are frequently accomplished via centrifugation and/or filtration procedures.

Flocculating agents can be employed to improve liquid/solid separations by aggregating the solids that are present in a protein suspension, thereby increasing the particle size of the solids (for review, see Halverson and Panzer, 1980). An increase in particle size is particularly beneficial in centrifugation and sedimentation applications where the particle sedimentation velocity is proportional to the square of the particle radius. The increased sedimentation velocity that results from larger particle sizes can improve productivity in any type of liquid/solid separation where particle sedimentation velocity is a factor.

SUMMARY OF THE INVENTION

This invention broadly concerns the separation of soluble proteins from insoluble contaminants via flocculation. More particularly, it relates to the use of anionic polymeric flocculants in the separation and recovery of somatotropin proteins.

Therefore, in accordance with one aspect of the present invention, there is provided a method for separating an aqueous protein suspension of soluble somatotropin monomer and insoluble contaminants by adding to the suspension an anionic polymer in an amount and under conditions effective to cause the flocculation of the insoluble contaminants. The flocculated, insoluble, material can be easily separated from the soluble somatotropin monomer to recover a clarified supernatant of soluble somatotropin monomer.

In accordance with another aspect of the invention, there is provided a method for the recovery of somatotropin monomer which comprises obtaining a mixture of somatotropin proteins comprising somatotropin monomer and somatotropin oligomer in aqueous solution at a pH greater than about 7;

producing a protein suspension containing soluble somatotropin monomer by precipitating a major portion of the somatotropin oligomer from the solution while maintaining a major portion of somatotropin monomer in solution by reducing the pH of the solution to less than about 6.5;

adding to the protein suspension containing soluble somatotropin monomer an anionic polymer in an amount and under conditions effective to cause the flocculation of the precipitated proteins; and separating the flocculated material from the solution of somatotropin monomer.

In accordance with another aspect of the invention, there is provided an aqueous protein suspension comprising somatotropin monomers, somatotropin oligomers (oligomer as used herein refers to dimers as well as other multimeric forms of the protein), and an anionic polymer.

Suitable anionic polymers used in accordance with the method of this invention include but are not limited to polyacrylamides, particularly those having charge densities in the range of about 1 to about 20%, and polysaccharides such as starch.

This invention provides an improved means for separating somatotropin monomer from the insoluble contaminants that are selectively precipitated from the monomer during recovery of the recombinant protein. Flocculation of the insoluble contaminants increases their particle sizes and therefore their sedimentation velocities, providing improved productivity in liquid/solid separations.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
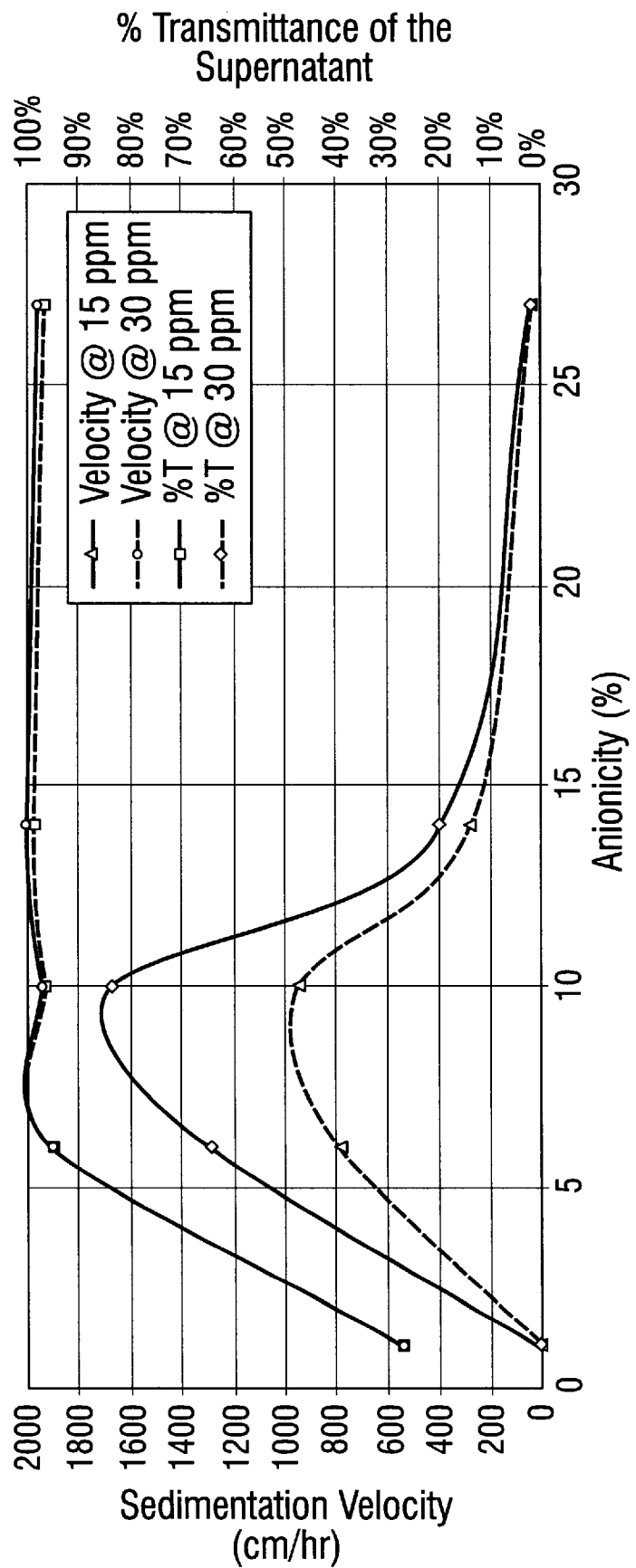
FIG. 1 illustrates the effect of polymer charge density on the flocculation performance.

This invention provides anionic polymeric flocculants for improving the efficiency of liquid/solid separations by increasing the particle size of insoluble contaminants in a protein suspension.

"Protein suspension," as used herein, represents an aqueous suspension, preferably at an acidic pH (i.e., less than about 7), which comprises soluble and insoluble components. Typically, but not necessarily, the soluble component includes the desired protein product (e.g. soluble somatotropin monomer) whereas the insoluble components include the undesired contaminants (e.g. somatotropin oligomers and bacterial cell debris). "Somatotropin" or "ST" refers to any polypeptide that has biological activity and/or chemical structure similar to that of a somatotropin produced in the pituitary gland of an animal. Such somatotropins include natural somatotropins produced by the pituitary somatotropic cells or, alternatively, somatotropins produced by recombinant DNA technology in which a somatotropin or a variant derived therefrom is expressed by genetically transformed prokaryotic or eukaryotic cells, e.g. bacteria (such as *E. coli*), yeast or algae.

"Refold solution" refers to the stock solution obtained as a result of the folding and oxidation in the somatotropin naturation step, as described for example in U.S. Pat. Nos. 4,511,502 and 4,652,630. Subsequent adjustment of the pH of the refold solution to below about 6.5, preferably to between about 4.0 and about 6.0, selectively precipitates the insoluble contaminants while leaving the soluble somatotropin monomer substantially unaffected.

"ST protein suspension" refers to the aqueous suspension produced essentially in accordance with U.S. Pat. No. 5,182,369, such that the suspension has a pH between about 4.0 and about 6.5 and comprises primarily soluble somatotropin monomer and insoluble contaminants. Prior to the pH precipitation, the solution generally contains from about 1 to about 30 grams/liter total protein comprising somatotropin, somatotropin aggregates and *E. coli* proteins. Approximately 40–60% of the total protein is typically precipitated in the pH adjustment step, resulting in an oxidized somatotropin monomer purity greater than about 90% in the liquid fraction.

"Flocculation" refers to the aggregation of insoluble particles caused by the addition of a suitable flocculating agent to a protein suspension. By increasing the particle size of the insoluble components present in the suspension, the efficiency of solid/liquid separations, such as by filtration or centrifugation, is improved.

"Clarification" refers to the removal of insoluble contaminants from a protein suspension, thereby improving the clarity/purity of the suspension, for example as measured by a decrease in the spectrophotometric absorbance of the suspension at 700 nm.

"Separation" refers to the removal of the aqueous phase, containing the soluble somatotropin monomers, from the insoluble particles following flocculation of the ST protein suspension. This removal is accomplished by any means compatible with the present invention including the common industrial methods such as sedimentation and filtration. This separation results in the recovery of a solution of somatotropin monomers which is essentially free of insoluble contaminants.

"Sedimentation" refers to the settling of the flocculated precipitated contaminants, either by centrifugation or by gravity.

The following art, to the extent that it provides exemplary procedural or other details supplementary to those set forth herein, is specifically incorporated herein by reference:

Garcia, F. A. P., "Protein Precipitation" in: Recovery of Biological Materials, John Wiley & Sons, 1993.

Gates et al., "Selecting Agitator Systems to Suspend Solids in Liquids", Chemical Engineering, May 24, 1976.

Halverson, F., Panzer, H. P., "Flocculating Agents" in: Encyclopedia of Chemical Technology, Volume 10, Third Edition, John Wiley & Sons, 1980, pp 489–523.

Muhle, K. and Domasch, K. "Stability of Particle Aggregates in Flocculation with Polymers", Chemical *Engineering Progress* 29 (1991).

Wurzburg O. B., "Modified Starches: Properties and Uses", CRC Press, Inc., pp. 4–98.

In one aspect of this invention, there are provided methods for improved liquid/solid separations of an aqueous ST protein suspension containing soluble proteinaceous product and insoluble contaminants. This method involves the clarification of a protein suspension by flocculation of the precipitated contaminants using anionic polymers. A suitable flocculant is dispersed in a protein suspension under conditions effective to cause the aggregation of the insoluble proteins and other contaminants present in the suspension while leaving the soluble product substantially unaffected. A number of advantages are provided by the flocculation procedure described herein. First, separation efficiency is improved due to the fact that the sedimentation velocity of solids increases with increasing particle size. This can effectively minimize or even eliminate the need for centrifugation in a solid/liquid separation, thereby reducing the capital costs associated with the process. Also, the method can improve filtration processes by reducing the pressure drop that is often observed across filters. This change in hydrodynamic properties can allow for higher flow rates and/or the use of less diatomaceous earth (i.e., filter aid) in filtration processes.

Flocculants for use in this invention include polymers having anionic charge characteristics effective to cause flocculation of insoluble material present in a protein suspension. One measure of anionic charge characteristic is charge density. Charge density is represented by the percent of monomer present on a given polymer that possess an anionic chemical group. Charge density can be uniform or non-uniform. For some acrylamide based polymers, the charged group is a carboxyl group that is associated with integrated acrylate molecules (i.e. acrylic acid in an unprotonated state). Acrylate monomer has nearly the same molecular weight and reactivity as the acrylamide monomer. Therefore, copolymerization with these molecules forms a polymer that has a near uniform distribution of the carboxyl groups. The molar ratio (expressed as a percentage) of the acrylate monomer to the total moles (of acrylate and acrylamide) is the charge density of that polymer. So a polymer having a 10% charge density has an acrylate composition of 10%.

Assessment of the anionic character (i.e. charge density) of an acrylamide polymer made by a copolymerization reaction can be reported in 2 ways. The first and more common practice is to report the molar percentage of the acrylate (which contains the anionic charge group) in the acrylamide-acrylate copolymerization reaction feed. This percentage is referred to as the "theoretical" anionicty or "theoretical" charge density. The other method of reporting anionic character is based on a titration method that measures the "total" charge density of the test polymer. This method includes not only the charge density contributions from the copolymerization reactants, but also includes the anionicity that results from hydrolysis of the amide group that occurs during the polymerization reaction. The hydrolysis reaction can convert a significant number of the amide groups to carboxyl groups, as much as 7% for low charge density polymers (as in the case of the Floerger AN 905 PWG polymer). In our experience, it is the total anionicity that dictates how well a given polymer performs in this process application. "Polymer charge density" or "polymer anionicity" herein is defined as the total charge density, which includes charge resulting from the copolymerization reaction (i.e. theoretical charge density), plus the charge contributions originating from hydrolysis.

The anionic features of the polymeric flocculants can be imparted by any appropriate chemical constituents present on the polymer. Anionic polymers containing carboxyl, carboxymethyl, phosphate and sulfate functionalities, for example, are particularly well suited for the invention. Examples of preferred flocculants according to this invention include anionic polyacrylamides and anionic polysaccharides.

Polyacrylamides with carboxyl groups represent one preferred class of flocculants for use in this invention. Those having polymer charge densities between about 1 and 30%, more preferably between about 1 and 20%, and most preferably between about 5 and 12% at neutral pH, have been found most suitable.

A flocculant used in this invention can have essentially any molecular weight provided it does not adversely effect the desired flocculation of the insoluble contaminants. Higher molecular weights may provide improved flocculation performance. Typically, the average molecular weight will be in the range from about 100,000 to 50,000,000 or more. Preferably it is greater than about 100,000, more preferably greater than about 1,000,000, and most preferably greater than about 10,000,000, provided this does not adversely effect the desired flocculation reaction.

In a preferred embodiment of this invention, a ST protein suspension is clarified by the above approach. U.S. Pat. No. 5,182,369, the disclosure of which is incorporated herein by reference, describes the selective precipitation of somatotropin oligomers and other contaminants as a means for the recovery of highly purified somatotropin monomer from a refold solution. This is accomplished by reducing the pH of the refold solution from the high level employed for the maturation step (usually in excess of pH 10) down to an optimum pH end point value that is generally in the range of about 4.0 to about 6.5.

The particles that result from the precipitation step are generally small and do not readily settle. Under gravitational conditions, a significant quantity of the solids stay suspended for an indefinite period of time such that a liquid/solid interface is not visually observable. The characteristically slow sedimentation velocity of this suspension makes clarification using centrifugation difficult. Depth filtration has also been used to clarify this process stream, but there are also disadvantages associated with this type of separation, such as the expense of additional raw materials and waste handling.

Although additional purification steps may be desired, for example by chromatographic or other methods, the ST monomer recovered in accordance with this invention is substantially free of residual bacterial protein and other contaminants and is suitable for administration to the target animal by injection or implantation without further purification. The purified product preferably contains less than about 10%, more preferably less than about 5% of somatotropin oligomers. Such oligomers are biologically inactive and do not result in any adverse reaction when administered to the target animal.

The mixing conditions used in the flocculation process can effect several parameters, as is known in the art. These parameters include the sedimentation rate of the flocs and the clarity of the supernatant. The preferred parameters with respect to mixing often represent a compromise designed to provide the optimal flocculation conditions possible in the face of frequently conflicting requirements of the individual parameters. For example, and increase in supernatant clarity is typically accompanied by a decrease in the sedimentation rate of the flocs.

Mixing of the polymer solution into the process pool can depend on not only the size, type, location, orientation and rotational speed of the mixer, but also can depend on the rate at which the polymer solution is delivered. So for a given impeller size, two parameters that can be manipulated include mixer rotational speed and the rate of polymer solution addition. The skilled individual in the art can readily determine the optimal conditions in this regard for a given product and process configuration.

A balance must be reached between agitation intensity and shear rate. The design of the mixing system used in accordance with this invention can assist in achieving this balance. A mixing impeller design that has a high pumping capacity and low shear rate is well suited for this application. For example, the Chemineer HE-3 high efficiency impeller (Chemineer—Dayton, Ohio) or the Lightnin A-310 high efficiency mixer impeller (Lightnin Mixers—Rochester, N.Y.) are suitable choices for this type of operation.

The mixer should also be capable of keeping the flocs suspended during the operation. The minimum level of agitation necessary in a flocculation system is bound by the fluid velocity needed to keep the formed flocs in a "just suspended state", so that solids are not allowed to settle at the bottom of the tank (Gates et al., 1976).

As alluded to above, two desirable features of the flocculation system described herein are good mixing and low shear. Tank design can to some extent address both of these concerns. Low shear can be met by minimizing the number of surfaces that cause shear by either creation of fluid motion or by surface particle interaction. Proper tank geometry and flocculant feed location will help ensure uniform mixing of the flocculant into the process fluids.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

The objective of the experiments described herein was to survey and identify flocculating agents that would aggregate the suspended particles from an aqueous suspension containing soluble and insoluble components. In this example, aqueous solutions of the flocculating agent were made up and added to the ST protein suspension. The flocculating agents were blended into this precipitate suspension using an overhead mixer as described in the Lab-Scale Flocculation Procedure #1. Upon completion of the flocculating agent addition, the mixer was stopped and the flocculated solids allowed to settle. The sedimentation velocity and supernatant clarity were then measured as described below:

Lab-Scale Flocculation Procedure #1

The experimental lab-scale flocculation equipment was assembled using a 4-liter glass beaker, a Lightnin® Lab-Master™ mixer with a 6.35 cm diameter A-310 high efficiency mixer impeller, an Ismatec peristaltic pump (model mv-ge) and a container for the polymer solution. The 4-liter glass beaker was baffled to enhance vertical mixing in the system. The 4-liter glass beaker was designed with glass indentions that ran from 1 cm above the bottom of the beaker to just below the lip of the beaker. The pump tubing size was selected based on the required feed flow rates for the polymer solution and a ⅛" stainless steel dip tube was used to feed the polymer solution. The outlet of this tube was located just below and just outside the impeller perimeter so as to ensure efficient mixing of the polymer into the process pool. The Ismatec pump was calibrated to obtain the desired polymer feed flow rate. A strip of tape with 1 cm increments marked on it was applied in a vertical position on the side of the 4-liter beaker to provide a means of measuring the level of the solid-liquid interface. The impeller was positioned approximately 3 to 4 cm above the bottom of the 4-liter beaker. The impeller position was fixed throughout a set of experiments by aligning the mixer chuck with a mark on the impeller shaft.

Two liters of the ST protein suspension were transferred to the 4-liter beaker, and then the mixer was turned on with the rotational speed set at 169 rpm. One liter of the polymer solution was pumped into the process pool at a constant rate over a 30 minute time frame. After delivery of the polymer solution into the process pool, the mixer was allowed to mix the contents for an additional 60 seconds and then the mixer was turned off. The settling rate of the flocculated particles and the supernatant absorbance were then measured. The results for a variety of flocculating agents are shown in Table 1.

Measurements

Sedimentation Velocity: Upon completion of the polymer solution addition to the precipitate solution, the mixer was stopped, and the flocculated solids were allowed to settle. After the initial momentum of the fluids diminished, the flocs began to settle and a visibly discrete solid-liquid interface is formed. Sedimentation velocity was measured by timing the change in the solid-liquid interface level. The timing started immediately after the mixer was stopped and the timer was stopped at a designated solid-liquid interface level in the glass vessel. The velocity at the interface represents the velocity of the slowest moving particles, which have sufficient concentration to be visible. The slowest moving particles are rate limiting with respect to cycle time and therefore are the most interesting in terms of characterizing the flocculation process. The accuracy of this measurement technique is dependent on the formation of a discernible solid-liquid interface and on the sedimentation velocity. The formation of large particles creates a situation where sedimentation rates are fast and where a discernible solid-liquid interface is not formed until the solids have settled to the bottom of the container. In such cases the measurement of sedimentation velocity is difficult and will likely have a larger margin of error.

Absorbance @700 nm: Measurement of the absorbance at 700 nm (A700) is a means of quantitatively assess the supernatant clarity achieved from a given treatment or process. The absorbance of a 1 ml sample of the supernatant after treatment was measured using a Hewlett Packard UV-VIS spectrophotometer (model 8453) and a cuvette with a 1 cm path length. The absorbance value obtained using this method can be converted to a transmittance value as per equation 14:

$$\%T=100\times\exp(-A_{700nm})$$

Intuitively, transmittance is easy to relate to clarity of the supernatant since it is directly related to clarity, whereas absorbance is inversely related to clarity. The clarification process of this invention results in a solution having $A_{700}$ less than 0.5, preferably less than 0.1.

TABLE 1

Survey of flocculating agents

| Flocculant Trade Name | Manufacturer | Characteristics: Composition | $MW_{ave}$ (Daltons) | Anion/Cationic | Theoretical Charged Group | Charge Density | Effectiveness (+/−) |
|---|---|---|---|---|---|---|---|
| STA-COTE H-44 | A. E. Staley Mfg. Co. | Corn Starch | | | | | − |
| STA-JEL 140 | A. E. Staley Mfg. Co. | Potato Starch | 1.5 M | Anionic | phosphate | | + |
| Floerger FA 920 | Chemtall, Inc. | Polyacrylamide | 15–20 M | Nonionic | | 0% | − |
| Floerger AH 912 | Chemtall, Inc. | Polyacrylamide | 15–20 M | Anionic | hydrolyzed homopolymer | ~2% | + |

TABLE 1-continued

Survey of flocculating agents

| Flocculant Trade Name | Manufacturer | Composition | MW$_{ave}$ (Daltons) | Anion/ Cationic | Theoretical Charged Group | Charge Density | Effectiveness (+/−) |
|---|---|---|---|---|---|---|---|
| Floerger AN 903 PWG/GR | Chemtall, Inc. | Polyacrylamide | 15–20 M | Anionic | carboxyl | 1.5% | ++ |
| Floerger AN 905 PWG/GR/VHM | Chemtall, Inc. | Polyacrylamide | 15–20 M | Anionic | carboxyl | 3% | ++ |
| Floerger AN 910 PWG | Chemtall, Inc. | Polyacrylamide | 15–20 M | Anionic | carboxyl | 10% | ++ |
| Floerger AN 923 PWG | Chemtall, Inc. | Polyacrylamide | 15–20 M | Anionic | carboxyl | 20% | + |
| Floerger AN 934 PWG | Chemtall, Inc. | Polyacrylamide | 15–20 M | Anionic | carboxyl | 30% | + |
| Agefloc WT601 | Ciba | Polyacrylamide | 15–20 M | Anionic | carboxyl | 10% | + |
| Agefloc WT611 | Ciba | Polyacrylamide | 15–20 M | Anionic | carboxyl | 10% | ++ |
| CYSEP 2411 | CYTEC, Inc. |  | ~6 M | Cationic |  |  | − |
| CYSEP 2709 | CYTEC, Inc. |  | ~4 M | Cationic |  |  | − |
| CYSEP 329 | CYTEC, Inc. | Polyamine | ~50 K | Cationic |  |  | − |
| CYSEP 349 | CYTEC, Inc. | Polyamine | ~250 K | Cationic |  |  | − |
| CYSEP 4022 | CYTEC, Inc. | PolyDADM | ~50 K | Cationic |  |  | − |
| CYSEP 615 | CYTEC, Inc. | Polyamine | ~30 K | Cationic |  |  | − |
| Methocel A4M PREM | Dow Chemical Co. | Methcellulose |  | Nonionic |  |  | − |
| Methocel E4M PREM | Dow Chemical Co. | Hydroxypropyl Methocellulose |  | Nonionic |  |  | − |
| Methocel F4M PREM | Dow Chemical Co. | Hydroxypropyl Methocellulose |  | Nonionic |  |  | − |
| Methocel K100M PREM | Dow Chemical Co. | Hydroxypropyl Methocellulose |  | Nonionic |  |  | − |
| Chitosan | SIGMA | Chitosan | ~370 K |  |  |  | − |
| Preastol 2500 TR | Stockhausen, Inc. | Polyacrylamide | 15–20 M | Nonionic |  | 0% | − |
| Preastol 2505 | Stockhausen, Inc. | Polyacrylamide | 15–20 M | Anionic | Carboxyl | 5% | + |
| Preastol 2515 TR | Stockhausen, Inc. | Polyacrylamide | 15–20 M | Anionic | Carboxyl | 15% | ++ |
| Preastol 2520 | Stockhausen, Inc. | Polyacrylamide | 15–20 M | Anionic | Carboxyl | 20% | + |

+=clear supernatant (% Transmittance ≥ 70%), slow sedimentation (velocity < 500 cm/hr)
++=clear supernatant (% Transmittance ≥ 95%), fast sedimentation (velocity ≥ 500 cm/hr); "NT" = not tested;
−=no visible formation of a solid-liquid interface; "M" = millions; "K" = thousands; MW = molecular weight These results show that only anionic flocculating agents produced detectable signs of flocculation as indicated by the sedimentation velocity of the flocculated solids and by the clarity (reported as % transmittance) of the aqueous phase (supernatant). Flocculating agents producing flocs that exhibited sedimentation velocities greater than 500 cm/hr and supernatants with % transmittance greater than 95% were given a rating of "++". Flocculating agents producing flocs that exhibited sedimentation velocities less than 500 cm/hr and supernatants with % transmittance greater than 70% were given a rating of "+". Flocculating agents producing no visible signs of flocculation, as indicated by the lack of formation of a liquid-solid were given a rating of "−". It should be noted that the reported charge densities for the respective flocculating agents are theoretical charge densities, and do not represent the total charge density.

EXAMPLE 2

A range of flocculating agent concentrations was evaluated using Lab-Scale Flocculation Procedure #2. A high molecular weight (roughly 16 million daltons) acrylamide polymer with anionic character was used in this evaluation. The three primary measurements of interest in these experiments were supernatant absorbance, total protein concentration and bST concentration. Table 2 displays the data obtained using this procedure. The final polymer concentration referred to herein represent the total polymer concentration after all of the polymer solution had been added to the ST protein suspension.

Lab-Scale Flocculation Procedure #2
1. Make up the flocculant solution at room temperature to the desired concentration (i.e. 200 ppm) 1 hour in advance of the flocculation experiments.
2. Label 3 polycarbonate conical-bottom test tubes (w/screw caps). Each polymer concentration was evaluated in triplicate.
3. Pipette the ST protein suspension into each test tube. Pipette the corresponding volume of the polymer solution into the ST protein suspension and then immediately cap the test tube and invert 20 times.
4. Place the test tubes into a bucket type centrifuge and spin at room temperature for 5 minutes at 1000 rpm (Centrifuge type: Sorvall RC5C, Rotor size: SS34, RCF~119).
5. After centrifugation, gently remove the cap and using a transfer pipette pull the top 6 ml (of 10 ml total) of supernatant. Draw liquid near the liquid/air interface while trying to avoid floating solids. Transfer the supernatant to a labeled test tube.
6. Measure the absorbance of the supernatant at 700 nm. Then dilute 1 ml of the supernatant in 5 ml of 1% acetic acid. Measure the absorbance at 280 nm and use the supernatant for HPLC analysis to determine bST concentration.

Repeat steps 2 through 6 for a range of polymer concentrations.

Measurements
  Total Protein Concentration: The total protein concentration was calculated from a measured absorbance at a wavelength of 278 nm on a diluted supernatant sample. Solutions of bST have an extinction coefficient (extinction coefficient, $\epsilon$, or molar absorptivity is defined as the constant of proportionality in Beer's law: $A=\epsilon bc$, where A is absorbance, b is pathlength, and c is the molarity of the absorbing species) of 0.651. The supernatant sample was diluted in 1% acetic acid to obtain a total protein concentration near 1.5 grams/liter. The use of acetic acid as the dilution buffer serves to dissolve any suspended solids not removed in the treatment. (The suspended solids not removed in the treatment are considered part of the supernatant. These solids must be dissolved so they do not interfere with the absorbance measurement at 278 nm.) For this measurement, a 1% acetic acid solution was used as the zero reference.

bST Concentration: A portion of the diluted sample from the total protein concentration measurement was placed into a vial and analyzed using reverse phase HPLC.

The first row of data in Table 2 are the data associated with a sample of the ST protein solution that was filtered through a 0.2 micron syringe filter. The syringe filter samples sample serves as a means to assess the interaction, if any, of the flocculating agent with the soluble ST protein. The second row of data in Table 2 are data associated with the "control". The control is a sample of ST protein suspension to which flocculating agent was not added.

procedure. Thus, although a preferred range of polymer concentrations based on these experiments was between about 5 and 100 ppm, the invention is operable at up to 1000 ppm or more of polymer. The observed decrease in bST concentration, at polymer concentrations greater than or equal to 500 ppm, may be an indication that the flocculant agent was interacting with bST and pulling it down with the other solids.

EXAMPLE 3

Polyacrylamide flocculating agents manufactured by Chemtall Inc. (Riceboro, Ga.) were evaluated. The trade name for the Chemtall flocculating agent tested in this example is Floerger AN 905 . Six lab-scale flocculation experiments were run each using 2 liters of ST protein suspension and 1 liter of flocculant solution. The flocculant solution was added to a mixed ST protein suspension at a constant flow rate over an approximate time frame of 30 to 40 minutes. The mixing conditions were held constant for this set of experiments so that the effect of the polymer concentration on the flocculation performance could be assessed. The sedimentation velocity was approximated by measuring the time it took for the liquid/solid interface to reach a fixed level in the glass beaker after the over-head mixer was turned off. Supernatant absorbance was measured using a spectrophotometer. Table 3 illustrates flocculation performance data for a range of Floerger An 905 PWG flocculant concentrations.

TABLE 2

Effect of Flocculant Polymer Dosage on the Centrifugal Clarification of pH Adjusted ST Protein Suspension

| Polymer Concentration (ppm) | Supernatant Absorbance (A700) | Supernatant Protein Concentration (g/L)* | bST Concentration (g/L)* | Yield (%) |
|---|---|---|---|---|
| 0 | 0.01 | 8.50 | 7.72 | 100% |
| 0 | 1.67 | 13.48 | 8.71 | 113% |
| 1 | 1.65 | 12.53 | 8.62 | 112% |
| 10 | 1.32 | 8.97 | 8.12 | 105% |
| 50 | 0.15 | 8.13 | 8.04 | 104% |
| 100 | 0.06 | 7.87 | 8.15 | 106% |
| 500 | 0.30 | 6.93 | 6.75 | 87% |
| 1000 | 0.67 | 2.35 | 3.18 | 41% |

*Note: Protein and bST concentrations are corrected for dilutions (i.e. they reflect predilution values).

The data show that the total protein concentration decreased, as did the supernatant absorbance, upon addition of the flocculating agent for final flocculating agent concentrations greater than 1 ppm, when compared to the control, while the soluble ST concentration remained relatively constant for samples that were treated with final flocculating agent concentrations less than 500 ppm. From these data we can conclude the following: 1) The flocculating agent did not exhibit significant interaction with the soluble ST protein so as to remove the soluble protein from solution for final flocculating agent concentrations less than 500 ppm. 2) The decrease in supernatant absorbance and the decrease in the total protein concentration indicates that the addition of the flocculating agent to the solution containing soluble ST protein and precipitated contaminants improved the sedimentation properties of the solids in this system. The increase in sedimentation performance is directly related to the size of the particles in this system, which can be attributed the flocculation activity of the flocculating agent. Flocculation as measured by monitoring the total protein concentration was observed to occur for flocculating agent concentrations as low as 1 ppm. Flocculating agent concentrations above 50 ppm yielded purities at or above 95%, but the bST concentration began to decrease for flocculating agent concentrations greater than about 100 ppm by this Table 3 shows the results generated when polymeric acrylamide flocculant with an average molecular weight of about 16 million daltons and a charge density of 10% (Floerger AN 905 GR [Lot #8S36839]) was added to the ST protein suspension to obtain final polymer concentrations ranging from 5 to 35 ppm . The mixer speed was 169 rpm, the tank diameter was 15.9 cm, temperature was about 20° C., mixer impeller pump capacity was 24 liters/minute, impeller diameter was 6.35 cm, and impeller tip speed was 56 cm/sec, with center mixing in a baffled container.

The data show that the sedimentation velocity increased with an increase in the final polymer concentration, while the supernatant transmittance decreased with an increase in final polymer concentration. The increase in sedimentation velocity is an expected outcome in that more polymer is available to form larger aggregates. The larger aggregates will settle faster as a result of their larger size.

TABLE 3

Effect Polymer Concentration on the Flocculation Performance

| Exp. # | bST Volume (L) | [AN905]$_0$ (ppm) | Polymer Volume Added (L) | [AN905]$_f$ (ppm) | Polymer Addition Time (min) | Initial Sedimentation Velocity (cm/hr) | Supernatant Absorbance ($\lambda$ = 700 nm) | Supernatant Transmittance (%) |
|---|---|---|---|---|---|---|---|---|
| 1 | 2 | 15 | 1 | 5 | 30 | 77 | 0.011 | 99% |
| 2 | | | | | 30 | 78 | 0.016 | 98% |
| 3 | | | | | 30 | 85 | 0.003 | 100% |
| | | | | | Average = | 80 | | 99% |
| | | | | | Std. Dev. = | 4 | | 0.63% |
| 4 | 2 | 45 | 1 | 15 | 30 | 989 | 0.026 | 97% |
| 5 | | | | | 30 | 1147 | 0.022 | 98% |
| 6 | | | | | 30 | 1042 | 0.022 | 98% |
| | | | | | Average = | 1059 | | 98% |
| | | | | | Std. Dev. = | 80 | | 0.25% |
| 7 | 2 | 75 | 1 | 25 | 30 | 1205 | 0.040 | 96% |
| 8 | | | | | 31 | 1266 | 0.039 | 96% |
| 9 | | | | | 30 | 1456 | 0.031 | 97% |
| | | | | | Average = | 1309 | | 96% |
| | | | | | Std. Dev. = | 131 | | 0.45% |
| 10 | 2 | 105 | 1 | 35 | 30 | 1603 | 0.047 | 95% |
| 11 | | | | | 30 | 1767 | 0.052 | 95% |
| 12 | | | | | 30 | 2231 | 0.038 | 96% |
| | | | | | Average = | 1685 | | 96% |
| | | | | | Std. Dev. = | 116 | | 0.70% |

Sedimentation velocity data point was not included in the average or std. dev. because the solids did not suspend at during the post mixing stage of the run. The flocculated contents were mixed for 1 minute after completion of the polymer addition.

EXAMPLE 4

Data on the effect of the polymer charge density on the flocculation performance is listed in Table 4. Two final polymer concentrations (15 ppm and 30 ppm) were evaluated using Chemtall flocculant polymers. The polymers used in this set of experiments had theoretical charge densities ranging from 0% to 20%. The reaction conditions were as follows: ST protein suspension volume=2 liters, mixer size, capacity, and speed as in EXAMPLE 3, tank diameter=15.9 cm, ⅛" dip tube, volume of polymer added=1 liter resulting in a 50% increase in volume.

TABLE 4

Summary of Chemtall Flocculant Evaluations

| Exp. # | Flocculant | Theoretical Anionicity (%) | Measured Anionicity (%) | [F]$_0$ (ppm) | [F]$_f$ (ppm) | Actual polymer addition time (min) | Pump speed setting | Initial sedimentation velocity (cm/hr) | Supernatant absorbance ($\lambda$ = 700 nm) | Transmittance (%) |
|---|---|---|---|---|---|---|---|---|---|---|
| 1 | Floerger FA 920 | 0 | 1 | 45 | 13 | 31 | 500 | 0 | 1.297 | 27% |
| 2 | Floerger AN 903 PWG | 1.5 | 6 | 45 | 15 | 32 | 500 | 785 | 0.053 | 95% |
| 3 | Floerger AN 905 PWG | 3 | 10 | 45 | 15 | 32 | 510 | 947 | 0.034 | 97% |
| 4 | Floerger AN 910 PWG | 10 | 14 | 45 | 15 | 32 | 520 | 275 | 0.017 | 98% |
| 5 | Floerger 923 AN PWG | 20 | 27 | 45 | 15 | 31 | 530 | 23 | 0.026 | 97% |
| 6 | Floerger FA 920 | 0 | 1 | 90 | 30 | | | 0 | 1.313 | 27% |
| 7 | Floerger AN 903 PWG | 1.5 | 6 | 90 | 30 | 31 | 540 | 1284 | 0.050 | 95% |
| 8 | Floerger AN 905 PWG | 3 | 10 | 90 | 30 | 31 | 540 | 1657 | 0.024 | 98% |
| 9 | Floerger AN 910 PWG | 10 | 14 | 90 | 30 | 32 | 540 | 391 | 0.002 | 100% |
| 10 | Floerger 923 AN PWG | 20 | 27 | 90 | 30 | | 550 | 25 | 0.026 | 97% |

The data in Table 4 was generated using Chemtall flocculating agents. These data were obtained using the Lab-Scale Flocculation Procedure #1. The sedimentation velocity and the supernatant transmittance data were plotted against the total polymer anionicity (as measured by the manufacturer), see FIG. 1. Table 4 lists data of the flocculation performance parameters with the actual measured polymer anionicity. Only anionic polymers manufactured using the acrylate and acrylamide polymerization were used to produce the data in Table 4 (as opposed to using anionic polymers that were made by hydrolysis). The theoretical anionicity is calculated by the amount of acrylate used in the copolymerization reaction. The total anionicity includes the theoretical anionicity, plus the anionicity resulting from hydrolysis.

The data in Table 4 show that polymeric flocculants that have an anionicity of 1% or lower did not exhibit detectable signs of flocculation as evidenced by the lack of formation of a visible solid-liquid interface at static conditions. The data points corresponding to a 1% anionicity represent the performance of a polymer that was manufactured as a nonionic polymer, that is, a polymer without carboxyl groups. The 1% anionic character of this polymer is the result of acid hydrolysis that occurred during the manufacturing process. The anionic character of a polymer containing carboxyl groups is significantly reduced at a low pH. This fact implies that a 1% anionic charge on the polymer at neutral pH (pH~7.0) is essentially neutralized (i.e. charge density≈0) at pH 4.5. For purposes of this discussion, the polymer associated with the 1% anionicity data points is considered as having a nonionic character. Formation of a solid-liquid interface did not occur at static conditions which suggests this polymer did not significantly affect the size of the precipitate particles in the suspension. Measurement of the solution clarity was essentially measurement of the diluted suspension since a separation of solids from the liquid did not occur, which explains the low transmittance value indicated in Table 4.

Flocculations performed using polymers with charge densities greater than 1% exhibited a discernible solid-liquid interface. The data clearly show that there exists an optimum anionicity for flocculation of the solids in this system. The 10% anionic polymer exhibited the fastest sedimentation velocity, which indicates that the optimum anionicity is near 10%. Sedimentation velocities obtained using polymers with charge densities less than or greater than the 10% anionic polymer were measurably slower than the velocity obtained when using the 10% anionic polymer, while the supernatant clarity appears to be relatively consistent for all flocculations performed using polymers with anionic character.

A polymeric flocculant with a charge density less than the optimal charge density (i.e. the 6% anionic polymer) exhibited a slower sedimentation velocity than the velocity achieved when using the 10% anionic polymer. The data indicate that charge densities less the optimal charge density result in less efficient flocculation of the solids.

EXAMPLE 5

The effect of the pH of the pH-adjusted ST protein suspension on flocculation performance was evaluated. The total protein concentration of refold concentrate was adjusted to approximately 20 g/L using purified water. The pH of the diluted refold solution was adjusted using 5% acetic acid to 4 different pH endpoints. At each pH a 2 liter sample of the resulting suspension was taken and further mixed for at a minimum of 1 hour using a stir bar and stir plate. Each of the suspension samples were flocculated using the Lab-Scale Flocculation Procedure #1 with a 1 liter aliquot of a 75 ppm solution of Floerger AN 905 PWG flocculating agent (Chemtall Inc., 10% anionicity). The dip tube diameter was ⅛", the mixer rotational speed was 169 rpm. The pH adjustment and the flocculations were run at room temperature (~23° C.). The pH data and the flocculation performance data is listed in the Tables 5 and 6 below. These data indicate that for the Floerger AN 905 PWG polyacrylamide flocculant (F905), the preferred pH of the pH-adjusted ST protein suspension is between about 4 and 5, more preferably between about 4.2 and 4.6.

TABLE 5

Flocculation Dependence on pH

| | | | | | Flocculation Performance | | |
|---|---|---|---|---|---|---|---|
| Exp. # | pH | Pump speed setting | $Q_P$ (ml/min) | Polymer addition time (min) | Initial Sedimentation velocity (cm/hr) | Supernatant Absorbance (700 nm) | % T |
| 1 | 4.73 | 600 | 37 | 27 | 504 | 0.032 | 97 |
| 2 | 4.60 | 600 | 37 | 27 | 932 | 0.053 | 95 |
| 3 | 4.50 | 600 | 37 | 27 | 1219 | 0.026 | 97 |
| 4 | 4.40 | 600 | 37 | 27 | 1477 | 0.023 | 98 |
| 5 | 4.30 | 600 | 37 | 27 | 1567 | 0.025 | 98 |

TABLE 6

Flocculation Dependence on pH

| | | | | | Flocculation Performance | | |
|---|---|---|---|---|---|---|---|
| Exp. # | pH | Pump speed setting | $Q_P$ (ml/min) | Polymer addition time (min) | Initial Sedimentation velocity (cm/hr) | Supernatant Absorbance (700 nm) | % T |
| 1 | 4.80 | 810 | 31 | 32 | 104 | 0.014 | 99 |
| 2 | 4.60 | 810 | 31 | 32 | 686 | 0.016 | 98 |
| 3 | 4.50 | 810 | 31 | 32 | 960 | 0.013 | 99 |

TABLE 6-continued

Flocculation Dependence on pH

| Exp. # | pH | Pump speed setting | $Q_P$ (ml/min) | Polymer addition time (min) | Flocculation Performance | | |
|---|---|---|---|---|---|---|---|
| | | | | | Initial Sedimentation velocity (cm/hr) | Supernatant Absorbance (700 nm) | % T |
| 4 | 4.40 | 810 | 31 | 32 | 1527 | 0.016 | 98 |
| 5 | 4.30 | 810 | 31 | 32 | 1292 | 0.009 | 99 |

Figure 2:
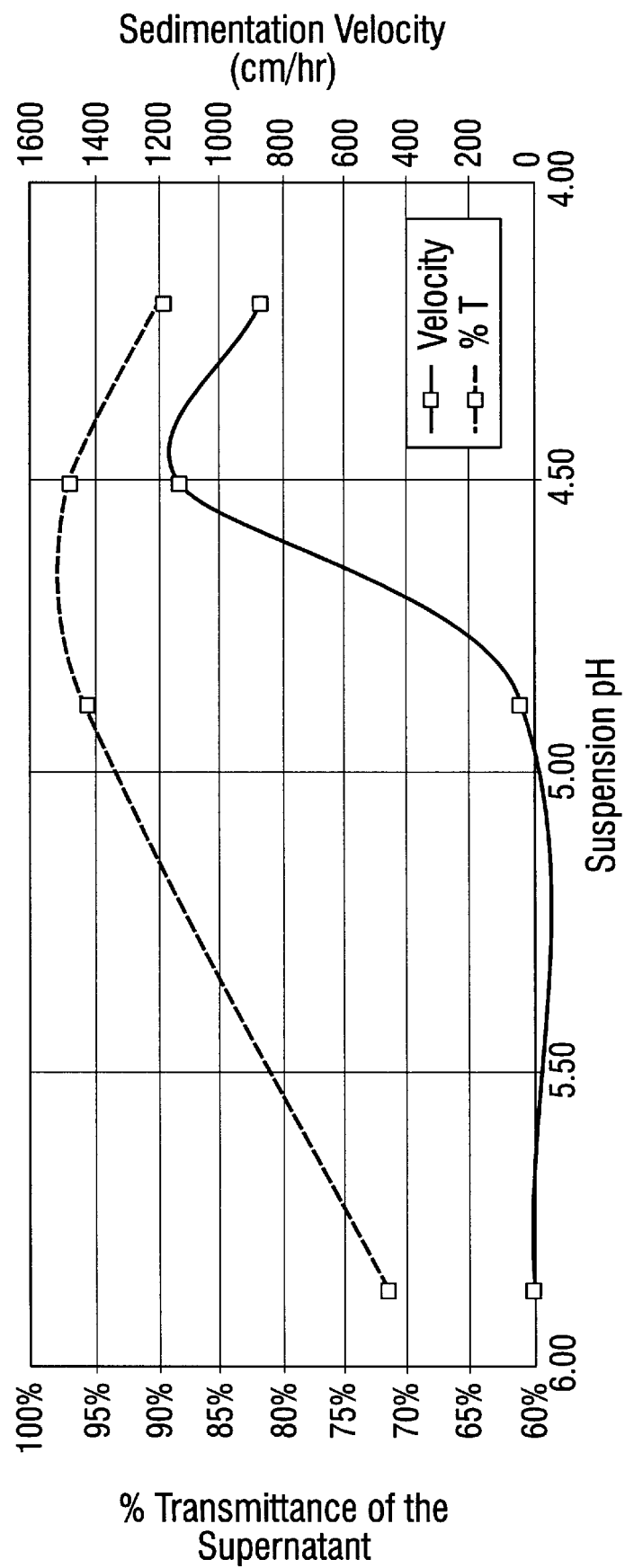
FIG. 2 illustrates the effect of pH on the flocculation performance from about pH 4.0 to about pH 6.0.
Figure 3:
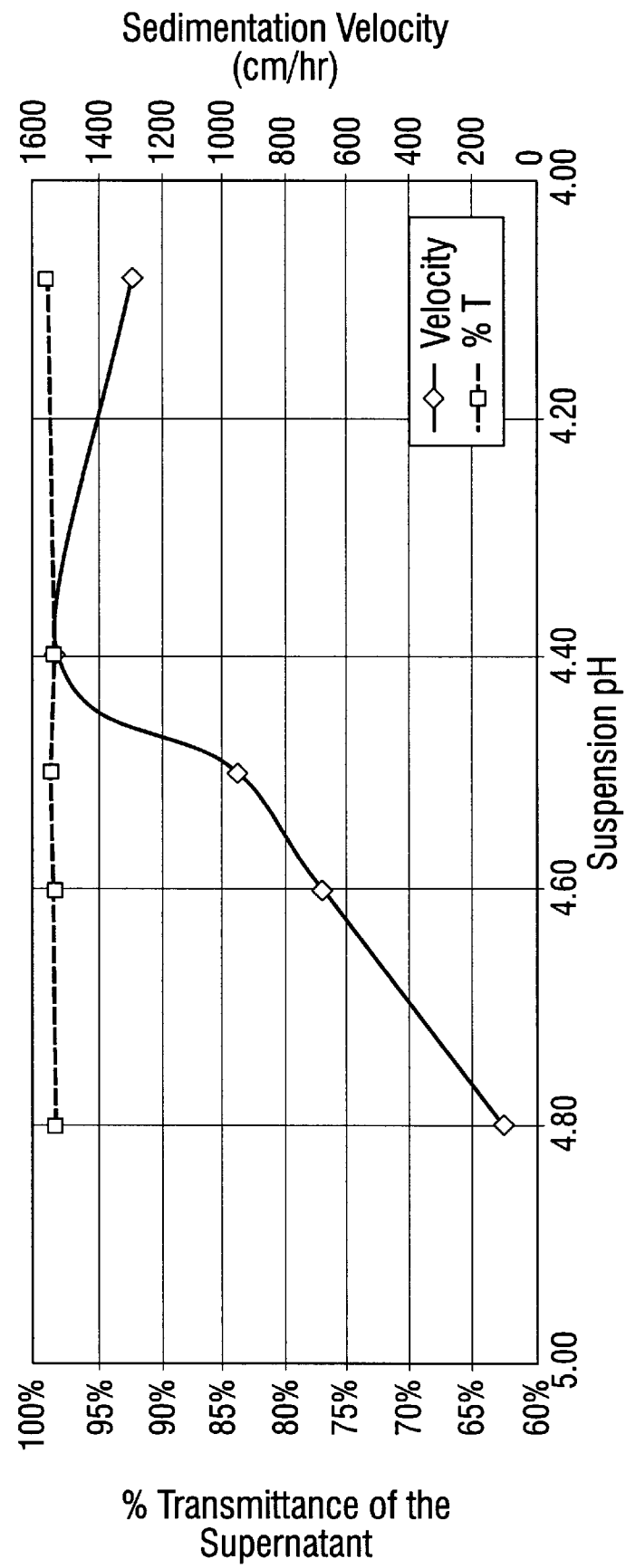
FIG. 3 illustrates the effect of pH on the flocculation performance from about pH 4.0 to about pH 4.8.

The data in Tables 5 and 6 show that flocculation performance, as measured by sedimentation velocity, is strongly dependent on solution pH. These data are represented in graphical form in FIGS. 2 and 3. The sedimentation velocity significantly increases as the pH decreases from 4.8 to 4.3. The clarity, as measured by % transmittance, of the supernatant in this pH range is relatively constant. The data in Tables 5 and 6 also indicate that for high molecular weight polymer of about 16,000,000 daltons, with a measured charge density of about 10%, the flocculation performance as measured by the sedimentation velocity is optimal near about pH 4.40.

EXAMPLE 6

A modified version of Lab-Scale Flocculation Procedure #2 was used to evaluate starch and cellulose polymers as flocculating agents. Essentially the same procedure was used as above except for the process volumes, beaker sizes and polymer addition times. In this experiment 1 liter of polymer was added to 1 liter of ST protein suspension over a 1 to 2 hour time frame.

Starch polymers were provided by A. E. Staley Manufacturing Company (Decatur, Ill.). One potato starch (Sta Jel 140, prejelatenized potato starch) were evaluated. The potato starch exhibited visual signs of particle aggregation under the conditions tested.

Sta Jel 140 is a prejelatenized potato starch, a starch which is primarily composed of amylose and amylopectin polymers. Amylose is linear polymer, whereas the amylopectin is a highly branched polymer. Most starches contain 18 to 28% amylose, with potato starch exhibiting amylose content at the lower end of this range (Wurzburg). Potato starch contains approximately 20% amylose and 80% amylopectin, and has an approximate average molecular weight of 1.5 million daltons. This ratio of amylose to amylopectin suggests that potato starch is a highly branched polymer. Unmodified potato starch naturally contains 0.08% phosphorous, which gives this starch its anionic characteristics.

Potato feed starch concentrations of 0.02% (wt/wt) and 0.2% (wt/wt) were tested to obtain final starch polymer concentrations of 0.01% (wt/wt) and 0.1% (wt/wt), respectively. In both cases the Sta Jel 140 potato starch exhibited visual signs of flocculation. The solids settled at gravitational conditions leaving a nearly crystal clear supernatant. The formed flocs were smaller than the flocs formed using the Floerger AN 905 PWG polymer, which resulted in slower sedimentation of the solids. Measurement of the total soluble protein indicated that there was no detectable loss in soluble protein concentration upon treatment of the ST protein suspension with the potato starch. This is evidence that the potato starch did not interact with the soluble bST protein.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for separating insoluble contaminants from an aqueous ST protein suspension, containing soluble somatotropin monomer, comprising:

a) adding to the ST protein suspension an anionic polymer in an amount and under conditions effective to cause the flocculation of the insoluble contaminants, and b) separating the flocculated insoluble contaminants from the supernatant containing soluble somatotropin monomer.

2. The method of claim 1, wherein the anionic polymer is a polyacrylamide; wherein the anionic polymer has a polymer charge density of less than about 30%.

3. The method of claim 1, wherein the anionic polymer has a polymer charge density between about 5% and about 12%.

4. The method of claim 1, wherein the anionic polymer has a polymer charge density between about 8% and about 11%.

5. The method of claim 1, wherein the anionic polymer's average molecular weight is greater than about 100,000; wherein the anionic polymer has a polymer charge density of less than about 30%.

6. The method of claim 1, wherein the anionic polymer's average molecular weight is greater than about 1,000,000.

7. The method of claim 1, wherein the anionic polymer's average molecular weight is greater than about 10,000,000.

8. The method of claim 2, wherein the anionic polymer has a polymer charge density between about 5% and about 12% and an average molecular weight greater than about 10,000,000.

9. The method of claim 1, wherein the anionic polymer is a polysaccharide.

10. The method of claim 9, wherein the polysaccharide is starch or modified cellulose.

11. The method of claim 9, wherein the polysaccharide is potato starch.

12. The method of claim 1, wherein the anionic polymer is present in the ST protein suspension at a concentration between about 1 and about 1000 ppm; wherein the anionic polymer has a polymer charge density of less than about 30%.

13. The method of claim 1, wherein the anionic polymer is present in the ST protein suspension at a concentration between about 10 and about 100 ppm.

14. The method of claim 1, wherein the anionic polymer is present in the ST protein suspension at a concentration between about 20 and about 30 ppm.

15. The method of claim 1, wherein the pH of the ST protein suspension is between about 4.0 and about 6.5.

16. The method of claim 1, wherein the somatotropin monomer is bovine somatotropin monomer; wherein the anionic polymer has a polymer charge density of less than about 30%.

17. The method of claim 1, wherein the flocculated contaminants are separated from the soluble somatotropin monomer by centrifugation, filtration, sedimentation, or combinations thereof.

18. The method of claim 1, wherein the ST protein suspension has a pH between about 4 and about 5 and wherein the anionic polymer is a polyacrylamide present in an amount from about 1 ppm to about 100 ppm having a polymer charge density from about 5% to about 12% and an average molecular weight greater than about 1,000,000.

19. A method for the recovery of somatotropin monomer which comprises:
   a) obtaining a mixture of somatotropin proteins comprising somatotropin monomer and somatotropin oligomer in aqueous solution at a pH greater than about 7;
   b) producing an ST protein suspension containing soluble somatotropin monomer by precipitating a major portion of the somatotropin oligomer from the solution while maintaining a major portion of somatotropin monomer in solution by reducing the pH of the solution to less than about 6.5;
   c) adding to the ST protein suspension an anionic polymer in an amount and under conditions effective to cause the flocculation of the precipitated proteins;
   d) separating the flocculated material from the solution of somatotropin monomer; and
   e) recovering the somatotropin monomer solution.

20. The method of claim 19, wherein the anionic polymer is a polyacrylamide; wherein the anionic polymer has a polymer charge density of less than about 30%.

21. The method of claim 19, wherein the anionic polymer has a polymer charge density between about 5% and about 12%.

22. The method of claim 19, wherein the anionic polymer has a polymer charge density between about 8% and about 11%.

23. The method of claim 19, wherein the anionic polymer's average molecular weight is greater than about 100,000; wherein the anionic polymer has a polymer charge density of less than about 30%.

24. The method of claim 19, wherein the anionic polymer's average molecular weight is greater than about 1,000,000.

25. The method of claim 19, wherein the anionic polymer's average molecular weight is greater than about 10,000,000.

26. The method of claim 19, wherein the anionic polymer has a polymer charge density between about 5% and about 12% and an average molecular weight greater than about 10,000,000.

27. The method of claim 19, wherein the anionic polymer is a polysaccharide.

28. The method of claim 27, wherein the polysaccharide is starch or modified cellulose.

29. The method of claim 27, wherein the polysaccharide is potato starch.

30. The method of claim 19, wherein the anionic polymer is present in the ST protein suspension at a concentration between about 1 and about 1000 ppm; wherein the anionic polymer has a polymer charge density of less than about 30%.

31. The method of claim 19, wherein the anionic polymer is present in the ST protein suspension at a concentration between about 10 and about 100 ppm.

32. The method of claim 19, wherein the anionic polymer is present in the ST protein suspension at a concentration between about 20 and about 30 ppm.

33. The method of claim 19, wherein the somatotropin is bovine somatotropin wherein the anionic polymer has a polymer charge density of less than about 30%.

34. The method of claim 19, wherein the flocculated material is separated from the soluble somatotropin monomer by centrifugation, filtration, sedimentation, or combinations thereof.

35. The method of claim 19, wherein the pH of the ST protein suspension is between about 4 and about 5 and wherein the anionic polymer is a polyacrylamide present in an amount from about 1 to about 100 ppm, having a polymer charge density from about 5% to about 12% and an average molecular weight greater than about 1,000,000.

* * * * *

UNITED STATES PATENT AND TRADEMARK OFFICE
CERTIFICATE OF CORRECTION

PATENT NO.    : 6,307,013 B1
DATED         : October 23, 2001
INVENTOR(S)   : Mark L. Chivers It is certified that error appears in the above-identified patent and that said Letters Patent is hereby corrected as shown below:

Column 18,
Line 36, before "in an amount" insert -- having a polymer charge density of less than about 30% --.

Column 19,
Line 40, before "in an amount" insert -- having a polymer charge density of less than about 30% --.

Signed and Sealed this

Seventh Day of May, 2002

Attest:

JAMES E. ROGAN
*Attesting Officer*   *Director of the United States Patent and Trademark Office*